(12) United States Patent
Freitag et al.

(10) Patent No.: US 6,258,275 B1
(45) Date of Patent: Jul. 10, 2001

(54) AFFINITY MACROLIGANDS (75) Inventors: Ruth Freitag, St. Sulpice; Frédéric Garret-Flaudy, Morges, both of (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/411,148

(22) Filed: Oct. 1, 1999

(51) Int. Cl.$^7$ .............................. B01D 43/00; C08H 1/00; C08F 8/00

(52) U.S. Cl. .......................... 210/632; 210/660; 210/690; 435/180; 524/498; 524/797; 525/54.1; 525/54.11; 525/329.4; 525/385; 527/202

(58) Field of Search ........................... 210/632, 732–734, 210/735, 660, 666, 690; 252/180; 502/402; 524/498, 797; 525/54.1, 54.11, 54.2, 329.4, 385; 527/200–203, 207; 528/493, 497, 502, 494; 435/177, 180

(56) References Cited

U.S. PATENT DOCUMENTS 3,336,269 * 8/1967 Monagle et al. .
3,509,113 * 4/1970 Monagle et al. .
4,822,848 * 4/1989 Ito et al. .
4,973,554 * 11/1990 Luong et al. .

(List continued on next page.)

OTHER PUBLICATIONS

Freitag, R., "Reversibly water–soluble affinity macroligands for bioseparation", Current Trends in Polymer Science, 3: 63–79 (1998).

Eggert, M. et al., "Poly–N,N–diethlacrylamide Prepared by Group Transfer Polymerzation: Synthesis, Characterization, and Solution Properties", J. Polymer Science: Part A: Polymer Chemistry, 32: 803–813 (1994).

Freitag, R. et al., "A Comparison of Thermoreactive Water–Soluble Poly–N,N–diethylacrylamide Prepared by Anionic and by Group Transfer Polymerization", J. Polymer Science: Part A: Polymer Chemistry, 32: 3019–3030 (1994).

Freitag, R. et al., et al. "Synthesis and characterization of a highly uniform, thermosensitive affinity macroligand precursor suitable for carbodiimid coupling", Bioseparation, 4: 353–367 (1994).

Eggert, M. et al., "Affinity precipitation—an alternative to fluidized bed adsorption", J. of Chromatography A, 827: 269–280 (1998).

Chen, G. et al., "Preparation and Properties of Thermoreversible, Phase–Separating Enzyme–Oligo (N–isopropylacrylamide) Conjugates", Bioconjugate Chem., 4: 509–514 (1993).

Ding, Z. et al., "Synthesis and Purification of Thermally Sensitive Oligomer–Enzyme Conjugates of Poly (N–isopropylacrylamide)–Trypsin", Bioconjugate Chem., 7: 121–125 (1996).

Takei, Y. et al., "Temperature–Responsive Bioconjugates. 1. Synthesis of Temperature–Responsive Oligomers with Reactive End Groups and Their Coupling to Biomolecules", Bioconjugate Chem., 4: 42–46 (1993).

(List continued on next page.)

* cited by examiner

Primary Examiner—David A. Simmons
Assistant Examiner—Fred Prince
(74) Attorney, Agent, or Firm—Dann Dorfman Herrell and Skillman, P.C.

(57) ABSTRACT

Affinity macroligands (AML) comprising a reversibly water soluble poly-N-alkylacrylamide linked to a ligand, and their use in the separation of a target substance from a mixture comprising the target substance and other materials are disclosed. Preferred AMLs have number average molar masses of less than 7,000 g/mol (chain length n typically about 25), mass distributions of less than 1.2 and narrow precipitation-solubility temperature (NPST) interval, typically in the range of 1–2° C.

17 Claims, 5 Drawing Sheets

U.S. PATENT DOCUMENTS

| | | | |
|---|---|---|---|
| 5,013,669 | * | 5/1991 | Peters, Jr. et al. . |
| 5,108,622 | * | 4/1992 | Liao et al. . |
| 5,162,582 | * | 11/1992 | Ito et al. . |
| 5,310,786 | * | 5/1994 | Vorlop et al. . |
| 5,998,588 | * | 12/1999 | Hoffman et al. . |

OTHER PUBLICATIONS

Hoshino, K. et al., "Preparation of a New Thermo–Responsive Adsorbent with Maltose as a Ligand and Its Application to Affinity Precipitation", Biotechnology and Bioengineering, 60(5): 568 (1998).

Takei, Y.G. et al., "Temperature–Responsive Bioconjugates. 3. Antibody–Poly(N–isopropylacrylamide) Conjugates for Temperature–Modulated Precipitations and Affinity Bioseparations", Bioconjugate Chem., 5: 577–582 (1994).

Umeno, D. et al., "Water–Soluble Conjugate of Double–Stranded DNA and Poly(N–isopropylacrylamide) for One–Pot Affinity Precipitation Separation of DNA–Binding Proteins", Bioconjugate Chem., 9: 719–724 (1998).

Fong, R.B. et al., Thermoprecipitation of Streptavidin via Oligonucleotide–Mediated Self–Assembly with Poly(N–isopropylacrylamide), Bioconjugate Chem., 10: 720–725 (1999).

AFFINITY MACROLIGANDS

FIELD OF THE INVENTION

The present invention relates to affinity macroligands (AML), and in particular to AMLs comprising a reversibly water soluble polymer linked to a ligand, and their use in the separation of a target substance from a mixture comprising the target substance and other materials. The invention further relates to the polymers used to make AMLs and to processes for making the polymers and the AMLs.

BACKGROUND OF THE INVENTION

The purification and separation of the products of biotechnological processes from the impurities and contaminants present from their production is a challenging problem in the art. Firstly, the target substances are often fragile and easily denatured biopolymers, preventing the use of conventional separation techniques employing harsh non-physiological conditions such as elevated temperatures, organic solvents or extreme pH. Further, the scale of such processes is often smaller than the conventional pharmaceutical industry, throughput and speed is often important in view of need to maintain biological activity, and the impurities and contaminants typically need to be reduced to very low levels prior to the product's intended use.

Affinity separation is based on some form of interaction between members of a specific binding pair and makes use of one of these specific interactions to force a target substance into a second phase not easily accessible to the majority of the contaminants and impurities present in the reaction mixture.

Probably the best known of these techniques is affinity chromatography in which one member of a specific binding pair is immobilised on a solid phase column. When the reaction mixture is passed through the column, only the target substance binds to the immobilised ligand, while contaminants and impurities are flushed through the column unretained. Affinity chromatography combines specificity and high enrichment factors and has been used successfully in a number of biotech downstream processes. However, it suffers from limited scale-up potential, high equipment and material costs and incompatibility with many raw feeds due to the problem of the column clogging, particularly in the early stages of product isolation.

A number of alternatives to affinity chromatography have been proposed including affinity precipitation, a term used to describe two different types of separation procedures. In so-called primary effect affinity precipitation, the affinity reaction is the direct cause for the ensuing precipitation. This method calls for at least bivalent reagents. As the affinity interaction takes place, larger and larger associates are formed which precipitate once a certain size has been surpassed which is no longer compatible with dissolution.

However, the limits of this type of process are also immediately apparent. The application range is restricted to target substances having at least two binding sites and the concentration of the target substance in a given feed must be fairly well known beforehand, since both too high or too low a concentration will result in the formation of only small associates which tend to stay in solution. In addition, there have been problems in recovering the target substance from the complexes and it can be difficult to recycle the reagents used in the process.

In secondary effect affinity precipitation, the second phase required for the separation is created by a precipitation event which is independent of the affinity interaction. This affinity interaction simply ensures the preferential transfer of the target substance into the second phase. This requires the use of bifunctional reagents, so-called affinity macroligands or AMLs comprising a reversibly soluble polymer coupled to a ligand which is a specific binding partner of the target substance. These polymers are carefully chosen for their peculiar solubility. After the target substance has bound by affinity interaction to the AML via the ligand, the entire affinity complex can be precipitated by changing a critical solution parameter such as temperature, pH, salt concentration or combinations thereof. For thermoprecipitation from aqueous solution, the LCST (lower critical solution temperature) is usually exploited, increasing the temperature of the solution to cause precipitation of the AML [1].

Previously, Freitag et al [2–5] have reported that low molar mass poly-N,N'-diethylacrylamide with molar mass distributions of less than 2 can be synthesized employing living anionic, group transfer or radical polymerization reactions in the presence of a chain transfer agent. However, when living anionic polymerization using butyl-lithium as initiator is employed, the final polymer sequences contain no reactive site for affinity ligand coupling. However, the alternative synthesis of poly-N,N'-diethylacrylamide with a carboxylic acid end group by group transfer polymerization suffers from the disadvantages that the reaction is laborious, expensive and has a very low conversion rate.

Freitag et al [4,5] have also reported that pivalyl-m-aminophenylboric acid attached via carbodiimide coupling to the carboxylic acid groups of poly-N,N'-diethylacrylamide synthesized by group transfer polymerization reaction followed by ester hydrolysis is an affinity macroligand for "Substilisin Carlsberg". In this case, the specific binding between the neutral form of phenylboric acid and the serine residue of the active enzyme centre was involved. However, it was only shown that after affinity precipitation the enzyme activity in the supernatant was reduced by 30%.

Hoffman et al [6,7] and Sakurai et al [8] have reported on the synthesis of poly-N-isopropylacrylamide with a carboxylic acid end group using 3-mercaptopropionic acid (MPA) as chain transfer agent.

In Hoffman et al [6], a poly-N-isopropylacrylamide (Mn=4,000; n=34) is disclosed which is used to make enzyme conjugates, rather than AMLs. Further, the paper indicates that this polymer would not be suitable for use in an AML as the authors observed significant loss of the conjugate after 7 cycles of precipitation-dissolution.

In the case of Hoffmann et al [7], the polymers disclosed have number molecular masses Mn greater than 4,900 (n=42).

Sakurai et al [8] have described the production of 7 poly-N-isopropylacrylamides with Mw between 1,400 and 12,300 (n=12–108) and D between 1.20 and 1.94. There is no discussion about making AMLs with these polymers and the data in the paper for polymers with low Mn (e.g. Mn=2,150; n=18; D=1.26) shows that these polymers were incompletely recovered from aqueous solution even with centrifugation, indicating that they would not be useful in the production of AMLs.

Sasakura et al [9] reported the synthesis of seven polymers with Mn between 814 and 11,480 (corresponding to n=6–91) and polydispersities between 1.18 and 2.09. In this paper, a single AML with maltose was made with one of the higher molecular mass polymers (MW=12,800; Mn=7,442, n=59) and tested in the separation of Con A. This AML had an LCST of 4° C. and a NPST of 4° C. The paper further discloses that it was not possible to completely recover by centrifugation polymers with lower molecular masses, e.g. showing incomplete recovery of a polymer having Mn=5,443/n=43, indicating that such polymers would not be useful in the production of AMLs.

The ideal AML comprises a reversibly precipitable polymer and a ligand capable of specific interaction with the target substance as compared to other components of the reaction mixture. Typically, as the binding of the polymer to the ligand is covalent, the base polymer needs to carry activated sites which can be reacted with the ligand. Terminal end group polymers are favoured because in this case the affinity ligand is freely accessible, and maximum activity is retained. Further, the binding sites of the ligand need to have a high degree of uniformity so that there is little variance in the interaction energy of the AML and the target substance, helping to ensure that the precipitation of both the pure AML and AML target substance complex is uniform and well defined (quantitative precipitation within a narrow temperature window) without occurrence of fractionation. Low molecular mass of the polymer may result in high ligand density. In addition to these properties, the polymer also needs to be inert with respect to ligand, target substance and impurities interaction (low non-specific interaction). For industrial use, the precipitation and resolubilization cycles should be reproducible through multiple cycles within a narrow temperature range, be substantially independent of environmental conditions and provide a high level of recovery of the AML and the target substance.

However, to date, the AMLs in the art have failed to deliver the required properties, particularly for use in the context of a robust industrial process. This means that affinity precipitation using prior art AMLs needs to be performed under highly standardized conditions, making the technique inflexible and difficult to use.

SUMMARY OF THE INVENTION

Broadly, the present invention relates to poly-N-alkylcrlamides having properties which make them well suited for use as an affinity macroligands (AMLs). The present invention further relates to AMLs including these polymer and to methods for making the polymer, especially using chain transfer polymerization, and the AMLs. In still further aspects, the present invention relates to the use of the AMLs in separating a target substance from a mixture including it.

Accordingly, in a first aspect, the present invention provides a reversibly water soluble poly-N-alkylcrylamide having a homopolymeric chain of repeating units represented by the one of the following formulae:

wherein:
X is a reactive group;
$R_1$ and $R_2$ are independently selected from the group consisting of: hydrogen, $—CH_3$, $—CH_2CH_3$, $—CH_2CH_2CH_3$, $—CH(CH_3)_2$, $—CH_2CH(CH_2CH_3)_2$, $—CH_2CH_2OCH_3$, $—(CH_2)_3OCH_3$, $—(CH_2)_3OCH_2CH_3$, $—(CH_2)_3OCH(CH_3)_2$, $—C(CH_3)_2CONHR_4$ where $R_4=—CH_3$, $—CH_2CH_3$, $—CH(CH_3)_2$, $—CH_2CH_2OCH_3$, $—(CH_2)_3$, $—CH_2CH(OCH_3)_2$, and $—CH_2CH(OCH_2CH_3)_2$;

$R_3$ is selected from the group consisting of $—N(CH_2)_4$ (pyrrolidinyl), $—N(CH_2)_5$ (piperidinyl), and $—O(CH_2)_3OH$.

wherein n is an integer between 5 and 40 and the polymer has:
(a) a number average molar mass (Mn) of less than 11,300 g/mol;
(b) a mass distribution (D) of less than 2.0; and,
(c) a narrow precipitation-solubility temperature (NPST) interval of less than 3° C.

Conveniently, X is a group which is capable of reaction with a ligand to form an affinity macroligand (AML) by covalent bonding. Examples of reactive groups include carboxylic acids, aldehydes, esters, amines, alcohols and thiols. Preferred X groups are selected from the group consisting of: $—S—(CH_2)_y—COOH$, $—S—(CH_2)_y—CHO$, $—S—(CH_2)_y—NH_2$, $—S—(CH_2)_y—OH$, $—S—(CH_2)_y—SH$, $—S—(CH_2)_y—CH_3$, and their isomers, where y is an integer between 1 and 4. Still more preferably, X is selected from the group consisting of $—S—(CH_2)_2—COOH$, $—S—(CH_2)_2—NH_2$, $—S—(CH_2)_2—OH$, $—S—(CH_2)_2—SH$, and $—S—(CH_2)_2—CH_3$.

In preferred embodiments, the polymer is substantially homogeneous and is linear with the reactive group present at a terminal end of the polymer chain. These features help to ensure easy accessibility and high activity for ligand coupling, and helps to ensure that when the reactive group is linked to a ligand, the environment of the ligand on different polymer molecules is substantially the same, with the result that the reaction energy with the target substance is closely defined, providing a NPST of less than 5° C. and more preferably less than 2° C.

Preferably, the base poly-N-alkylacrylamide polymers of the invention may have one or more of the following properties:
(a) a number average molar mass of between 500 g/mol and 8,600 g/mol (n is about 30), more preferably with a molar mass of less than 5,900 g/mol (n is about 20), more preferably less than 5,000 g/mol, more preferably less than 2,900 g/mol (n is about 10).
(b) a number of monomer units in the polymer of preferably less than n=35, more preferably less than n=30, more preferably less than n=20 and most preferably less than n=10.
(c) a preferred mass distributions of ≦1.5, and more preferably ≦1.4, more preferably ≦1.3, more preferably ≦1.2, and most preferably between about 1.0 and 1.18.
(d) a preferred NPST between 1 and 2° C.
(e) a preferred LSCT in water between 4 and 80° C., more preferably between 20 and 60° C., and still more preferably between 25 and 40° C.
(f) recovery of the base polymer or AML comprising the polymer of greater than 80%, and more preferably greater than 90%, from aqueous solution after 5 or more precipitation-dissolution cycles at 1 wt % polymer and a centrifugal force of 10,000 g.

Examples of preferred polymers of the invention are given in the examples below. These include poly-N-isopropylacrylamide (LCST at 32.5° C.) and poly-N,N-diethylacrylamide (LCST at 33.3° C.) both of which have a number average molar mass of less than 5000 g/mol and can be synthesized by chain transfer polymerization using 3-mercaptopropionic acid (MPA). These polymers show a molar mass distribution of less or equal than 1.3 (determined by MALDI-MS), a very narrow precipitation temperature interval (<2° C.), and a reproducible narrow precipitation-solubility temperature interval (<2° C.). Preferably, the polymers of the invention have similar precipitation and solubility temperature intervals and do not show hysteresis (<4° C.) in solubility-precipitation cycles.

By way of example, in embodiments using the polymer poly-acryloylpyrrolidine, the chain length n correlates with the number average molecular mass Mn as follows: n=40, Mn=5,200 g/mol; n=35, Mn=4,510 g/mol; n=30, Mn=3,890 g/mol; n=25, Mn=3,260 g/mol.

In some embodiments, the NPST behaviour of the polymers is substantially independent of the environment parameters such as the presence of salt or cosolutes in the solution, i.e the presence of impurities or other chemicals does not substantially broaden the NPST range. This is a further advantage of these polymers as compared to prior art polymers whose NPST behaviour is dependent on such factors.

Preferably, the polymers are linear and highly homogeneous and have a heterotactic structure (determined by NMR), one reactive end group per polymer, and a pH independent, predictable and cosolute concentration depending LCST. Preferably, the polymers have on average one functional group X per molecule present at the end of the polymer chain.

In a further aspect, the present invention provides a process for producing a reversibly water soluble polymer poly-N-alkylacrylamide from monomer units, the process comprising:

(a) dissolving a corresponding monomer A, an initiator for the radical polymerization B, and a chain transfer agent C, in water or an organic solvent in a molar mass ratio A:B:C of 100:0.01–4:1–20;

(b) polymerizing the monomer under an oxygen free atmosphere at a temperature between 25° C. and the temperature of the boiling point at normal pressure of the solvent for 3 to 24 hours; and, (c) separating the polymer from unpolymerized monomer in a purification method comprising precipitation with organic solvents and/or ultra/diafiltration.

This process employing chain transfer polymerization allows the polymers to be synthesized in yields of more than 60–80%.

The preferred initiators for the radical polymerization are 2,2'-azoisobutyronitrile (AIBN), potassium-peroxodisulfate (KPS), and dibenzoylperoxide (BPO). The preferred organic solvents are methanol, tert-butanol, dimethylformamide, and tetrahydrofuran. The preferred chain transfer agent is selected from the list: HS—(CH$_2$)$_2$—E, where E represents a group of the list: COOH, NH$_2$, NH$_2$.HCl, OH, SH, CH$_3$. When organic solvents are used as the reaction medium for the polymerization step, preferably, they are moisture free in addition to being oxygen free.

Preferably, the separation is carried out as a sequence of steps including soluble-insoluble precipitation followed by filtration and drying under vacuum and/or by ultra/diafiltration followed by lyophilisation. Preferably, the precipitation steps use hexane or diethylether as the organic solvents. The inventors found that this procedure provided polymers that were not prone to the problem reported in the art of incomplete precipitation-solubility recycling of polymers.

The present inventors realised that polymers used to produce many prior art AMLs resulted from classical radical polymerization methods and so had average molar masses of up to 100,000 g/mol or higher and broad molar mass distributions, typically greater than 2. The prior art polymers were also highly heterogeneous in size and structure and the reactive site for ligand coupling was introduced either during polymerization through copolymerization of a suitable second monomer or afterwards by a statistical process called polymer analogous reactions. Both of these factors lead to increased heterogeneity of the polymer, the reactive site, and hence AMLs made by coupling ligands to the reactive sites of the polymer. As a result the behaviour of AMLs under process conditions becomes difficult to predict and affinity precipitation needs to be performed under highly standardized conditions. Furthermore, the ligands loses average activity, i.e. the affinity constant increases.

In a further aspect, the present invention provides an affinity macroligand (AML) comprising one of the above polymers coupled to a ligand. As indicated above, this provides AMLs useful for the separation of target substances which are specific binding partners of the ligand. The affinity macroligands can be represented by one of the following formulae, where L is a ligand and X' is the end group through which the ligand is attached to the polymer:

In affinity precipitation, the separation, enrichment or purification of the target substance is accomplished on the basis of the biospecific interaction or individual chemical structures of the target molecule. Affinity ligands represent complementary binding structures to the target substances. The selection of ligands is therefore determined by the specific and reversible binding affinity to the substance of interest. In order to create a suitable affinity macroligand, AML, a ligand must be coupled, typically covalently, via a functional group to the above mentioned polymer end group X without destroying the specific ligand binding activity and without strongly influencing the polymer solubility.

Conveniently, the ligand is selected from molecules such as an antibody or antigen, a receptor or polypeptide, an enzyme or coenzyme, substrate, or inhibitor, a carbohydrate, biotin and avidin, or nucleic acid (single or double stranded). In a further respect, the present invention relates to the synthesis of affinity macroligands of sufficiently high affinity by coupling the above mentioned affinity macroligand precursor to an affinity ligand. Preferably, the affinity constant for the interaction of the AML and target substance is less than or equal to $10^{-7}$ M.

Suitable ligands for use as part of AMLs are preferably chosen from:

(a) Antibodies or antigens, and fragments thereof such as Fc and Fab fragments.

(b) Enzymes or their coenzymes, substrates or inhibitors.

(c) Group specific ligands such as Protein A, Protein G, Protein L, (strept)avidin, lectins, or biomimetic dyes.

(d) Polypeptides, oligopeptides or amino acids.

(e) Hormones, receptors, inhibitors, effectors or cofactors.

(f) Sugars, polysaccharides or lipids.

(g) Vitamins and biotin, including its derivatives.

(h) Cells or cell surface receptors.

(i) Chelating agents such as iminodiacetic acid (IDA), TED, and EDTA and (Cu, Zn, Co, Ni, Ca, Cd, Hg, Fe, Mn)$^{2+}$.

(j) Nucleic acid molecules, either single or double stranded, and including DNA, cDNA, RNA, oligonucleotides and oligonucleosides, and derivatives of these species.

(k) Ligands capable of interacting in a similar manner with nucleic acids such as peptide nucleic acids (PNA).

In a further aspect, the present invention provides a process for preparing an affinity macroligand (AML), the process comprising reacting a ligand with the X group of a reversibly water soluble poly-N-alkylacrylamide as defined above. Preferably, the coupling is covalent, although other coupling methods such as the use of a non-covalent but high affinity interaction such as the (strept)avidin/biotin interaction may be employed to link the ligand to the polymer.

Techniques for linking the polymers of the invention to ligands, and especially biological ligands, are described in references such as Immobilized Affinity Ligand Techniques, Academic Press 1992, from Greg T. Hermanson, A. Krishna Mallia, and Paul K. Smith. Examples of useful techniques include:

(a) Esterification using N,N'-disuccinimidylcarbonate (DOC), N-hydroxysuccinimide (NHS)/1,3-dicyclohexylcarbodiimide (DOC), N,N'-carbonyl diimidazole (CD I), 1-ethyl-3(3-dimethylaminopropyl) carbodiimide (EDC), azlactone, iodo/bromo acetic acid, or succinimido-4-(N-maleimidomethyl) cyclohexane-1-carboxylate (SMCC).

(b) Substitution reactions using 2-fluoro-1-methylpyridinium toluene-4-sulfonate (FM), tosyl chloride, tresyl chloride, or cyanuric chloride (c) Addition reactions using cyanogen bromide, divinyl sulfone (DES) or epoxides.

(d) Reductive animations.

(d) Condensation reactions using hydrazones or hydrazides, or Manic reaction.

(e) Azo linkage using diazonium.

(f) Exchange reactions using Traut's/Elan's reagents.

(g) Disulfide formation via 2,2'-dipyridyldisulfide.

In some embodiments, the process for preparing the AML may comprise the additional step reacting the group X to produce a further group for coupling to the ligand.

In a further aspect, the present invention provides the use of an affinity macroligand as defined above for the purification of a substance which is capable of binding to the ligand. The AMLs can be used for the isolation, enrichment, or removal of target substances, which can be either products or impurities whose specific removal is desired.

In a further aspect, the present invention provides a process for purifying a target substance from a liquid containing a mixture of the target substance and other materials, the process employing an affinity macroligand comprising a reversibly water soluble polymer poly-N-alkylacrylamide as defined above which is linked to a ligand, wherein the ligand is capable of specifically binding to the target substance as compared to other materials in the mixture, the process comprising:

(a) contacting the AML with a liquid mixture under conditions in which the AML is soluble and the ligand can bind to the target substance;

(b) changing the temperature of the liquid to within the NPST range so that the AML precipitates, and/or adding a salt or cosolute; and, (c) separating the precipitated AML from the mixture.

In some cases where the amount of AML used is very low, it may be difficult to precipitate the AML bound to the target substance using changes in temperature or the addition of a salt or cosolute. In this situation, precipitation can be promoted by adding polymer or AML to the system to elevate the polymer concentration and so promote precipitation.

Optionally, and particularly where the target substance is a product rather than an impurity, the process comprises the further step of:

(d) recovering the target substance from the AML.

In some embodiments, having recovered the target substance from the AML, the process comprises the additional step of formulating the target substance in a composition.

Preferably, the target substances can be a bioproduct the separation of which is required from the matrix in which it has been produced, expressed or secreted, such as a cell culture, media or lysate. However, as mentioned above, the method is applicable to the removal of impurities from the mixture. Examples of applications of this type include the removal of endotoxin from DNA or RNA preparations using endotoxin binding proteins or the removal of protein A in the production of antibodies using protein A binding protein, antibodies or antibody fragments. Other applications of the invention in the removal of impurities or the isolation or enrichment of a useful target substance will be apparent to the skilled person following the teachings described herein.

After the target molecule has bound by affinity interaction to the AML via the affinity ligand, the entire affinity complex can be precipitated by changing a critical solution parameter, such as the temperature, the salt concentration, and combinations thereof. For thermoprecipitation from aqueous solution, the LCST (lower critical solution temperature) is usually exploited, i.e. the precipitation is achieved by increasing the temperature, optionally, in combination with other changes.

Embodiments of the invention will now be described by way of example with reference to the accompanying drawings.

BRIEF DESCRIPTION OF THE FIGURES

FIG. 4: Microcalorimetric endotherms of 1% (w/w) solutions of poly-NIPA N200 containing varied amounts of an additive: (a) $CaCl_2$ and (b) $Na_2SO_4$.

DETAILED DESCRIPTION

The work described herein summarizes investigations of the solubility of a number of poly-N-isopropylalkylacrylamides (poly-NIPA) and poly-N,N-diethylalkylacrylamides (poly-DEA) using microcalorimetric and optical measurements. The use of the polymers as AMLs is also investigated.

Material and Methods

Chemicals:

Chemicals were from Sigma, Fluka or Aldrich.

The highest available quality was used. 2,2'-azoisobutyronitrile (AIBN) was from Merck and N-isopropylalkylacrylamide (NIPA) from Polysciences or Aldrich. AIBN was recrystallized twice from ethylether prior to use. NIPA was recrystallized twice prior to use. The chain transfer agent 3-mercaptopropionic acid (MPA, Fluka) was purified by distillation under reduced pressure. Unless indicated otherwise, all other substances were used as obtained from the supplier.

Solvents such as ethylether, THF, and toluene were dried by boiling over Na-wire, kept under argon atmosphere afterwards and were freshly distilled whenever needed. Dry acetonitrile was obtained from Aldrich.

Molecular Mass Determinations:

The molecular mass distribution was determined by high molecular weight MS (MALDI-MS, matrix assisted laser desorption/ionization mass spectrometry) using a Vision 2000 (Finnigan MAT) or a LaserTec BT II (Vestec) respectively. 2,5-dihydroxybenzoic acid, α-cyano-4-hydroxycinnamic acid, and 4-hydroxy-3,5-methoxycinnamic acid were used as matrices with 6-desoxy-L-galactose as comatrix in the two latter cases. The positive ion mode was used throughout.

The apparent weight average of the molecular mass, Mw, and the apparent number average of the molecular mass, Mn, were calculated from the mass spectra using the following formulae:

$$Mw = \Sigma N_i M_i^2 / \Sigma N_i M_i \text{ and } Mn = \Sigma N_i M_i / \Sigma M_i$$

with $M_i$: mass of a given unimolecular oligomer species in a given sample and $N_i$: number of molecules of that mass in the preparation. The degree of polydispersity, D, was calculated as D=Mw/Mn. The average degree of polymerization, Pn, was calculated from Mn.

Turbidity Curves:

The transmission of an aqueous solution of a given polymer as a function of the temperature was measured at 500 nm on an Lambda 5 spectral photometer (Perkin Elmer) equipped with a PTP 1 thermostat (Perkin Elmer). Readings were taken every 6 seconds. Readings were taken for a temperature interval of 10° C. around the expected transition temperature. Heating rates were 0.5° C./min. The point of inflection of the S-shaped transmission curves (usually approximated as half-height or 50% transmission) was taken as cloud point.

Differential Scanning Calorimetry:

The DOC measurements were carried out using a high sensitivity differential scanning calorimeter (Polymer laboratories). Unless indicated otherwise, heating rates of 10° C./min and polymer concentrations of 1% (w/w) were used. The sample size was approximately 10 µl. The instrument calculates the heat of transition, $Q_{tr}$, per mg of polymer directly from the endotherms. From this, the calorimetric enthalpy, $\Delta H_{cal}$, can be calculated by a multiplication with the molecular mass. The number average of the molecular weight was used for this when known. In all other cases just the measured heat of transition is used.

Monomer Synthesis:

For the preparation of the monomer N,N-diethylalkylacrylamide, 112.5 g diethylamine were dissolved in 500 ml ethylether and placed under argon in a dry two-necked 1 L flask. The solution was cooled to around –2° C. and 55.7 g acryloylchloride were added drop-wise over the next 2 hours. A temperature below 3° C. was maintained. The final product was distilled in vacuum (1 mbar, 40° C.) from CaH$_2$. The yield was 74% and the purity was 100% (determined by GC). The pure and dry monomer was stored in a septum-sealed flask at –20° C.

Polymerization:

Details concerning the polymerization of both poly-N,N-diethylalkylacrylamide (Poly-DEA, R1 and R2) and poly-N-isopropylalkylacrylamide (Poly-NIPA, N1 and N2) in the presence of the chain transfer agent 3-mercaptopropionic acid (MPA) are compiled in Table 1. The radical starter (AIBN) was dissolved in methanol and placed in a two necked flask at 70° C. Afterwards the monomer and MPA were added. The mixture was refluxed for 21 hours and cooled to room temperature. After removal of the solvent by distillation the residue was dissolved in acetone, precipitated twice from petrolether and dried at ambient temperature in vacuum (10$^{-3}$ mbar) until constant weight.

For comparison the monomers were polymerized in the absence of the chain transfer agent (R100, N100, N200). In this case, the monomer was dissolved in dioxane (1 M) and the radical starter was added (1% mol$_{in}$:mol$_{mon}$). The mixture was heated to 50° C. and the reaction allowed to proceed for 45 min. Afterwards the product was recovered as described above.

Results and Discussion

Both poly-N,N-diethylalkylacrylamide (poly-DEA) and poly-N-isopropylalkylacrylamide (poly-NIPA) were investigated. Both polymers were produced by radical polymerization, controlling the molecular mass as well as the polydispersity using a chain transfer agent (3-mercaptopropionic acid, MPA). As a result of the chain transfer reaction, a carboxylic acid terminal reactive group is found on average in each of these polymers.

Characterization of the polymers:

Poly-NIPA is among the best investigated reversibly water-soluble polymers, with an LCST generally given between 29 and 34° C. Poly-DEA has been reported to have an LCST between 25 and 32° C. Most previous work has only considered radical polymers with high average molecular masses, and in the majority of the cases, the polymers are unfractionated preparations with high polydispersities.

The determination of the molecular mass and the mass distribution of the synthesized polymers in (aqueous) solution was made using high molecular weight mass spectrometry (MALDI-MS).

Since the distance between individual peaks corresponds to the mass of the respective repetitive units (127 g/mol for poly-DEA, 113 g/mol for Poly-NIPA), the MALDI-MS demonstrates that few if any side reactions occurred in the chain transfer polymerization used to make the polymers of the present invention. MALDI-MS is most reliable for molecules below 100,000 g/mol and we were not able to record relevant mass data for the large radical polymers of both types, i.e. polymers R100, N100 and N200 synthesized for comparison with the polymers produced using chain transfer polymerization.

Table 2 summarizes the mass data for the low molecular weight polymer preparations. Low polydispersities (<1.3) were calculated in all cases including the radical polymers prepared in the presence of the chain transfer agent MPA. The presence of a carboxylic acid end group in these molecules correlated well with the mass-to-charge ratios measured for the individual peaks. The presence of a carboxylic acid function in these molecules was in addition verified by titration and FT-IR measurements. The tacticity of polymers can be studied by high resolution $^1$H-NMR. An analysis of the tacticity of the polyalkylacrylamides prepared in investigation by 600 MHz $^1$H-NMR showed a heterotactic structure for the chain transfer polymers.

Turbidity Curves:

Most authors investigating high molecular weight, reversibly water-soluble polymers report only small changes of the precipitation temperature with increasing polymer concentration. A similar behaviour was observed for the low molecular mass polymers of the invention. Within the investigated range of 0.01% to 1.0% (w/w), the change of the precipitation temperature with the polymer concentration was negligible, i.e. less than 1° C. A 0.1% (w/w) solution of poly-DEA already sufficed to reduce the transmission to zero, while in the case of Poly-NIPA, the same result required at least a concentration of 1% (w/w). For comparison's sake, the optically determined precipitation temperatures summarized in Table 2 were measured for 1% solutions.

For (high molecular mass) poly-DEA an LCST of 32° C. has been published. The precipitation temperature of 31.4° C. measured for the high molecular weight sample R100 corresponds well to this value. Poly-DEA samples prepared by radical polymerization in the presence of the chain transfer agent, R1 and R2, have somewhat higher precipitation temperatures, i.e. 32.5 and 32.7° C. respectively. This inverse dependency of the critical temperature on the molecular mass has never been described for such small substances with a comparable extremely narrow mass distribution. The slightly higher precipitation temperature observed for R1 and R2 may conceivably be related to the fact that a carboxylic end group is present in these molecules but not in R100. However, in previous research such end group effects were ruled out for poly-DEA and certain derivatives thereof. In addition, no end group effect was observed for polymers N1, N2, and N100 respectively, see below.

Literature values for the LCST of Poly-NIPA vary between 32.0 and 34.3° C., although slightly higher values have been observed in isolated cases. The 33.2 and 34.0° C. measured in our investigations fall within that range, although poly-NIPA N1 and N2 were synthesized in the presence of the chain transfer agent, i.e. have small size and carry a carboxylic acid group. It has previously been shown that the presence and the charge status of such a carboxylic group have no influence on the precipitation temperature.

Effect of Solution Additives on the LCST:

From the point of view of a possible application of thermoprecipitable polymers as affinity macroligands, the cosolute effect is of major importance, since few reactions are carried out in pure water. The majority of putative biotechnological application will, for example, involve at least a buffered aqueous solution, most of these solutions will contain more than one active agent. For our investigations we chose NaCl as a fairly weak and $(NH_4)_2SO_4$ as one of the strongest salting out agents known. Both salts are typical components of biotechnical product matrices. Two polymers were chosen for the investigation of the cosolute effect, radical poly-DEA R100, and radical poly-NIPA N1.

Figure 1:
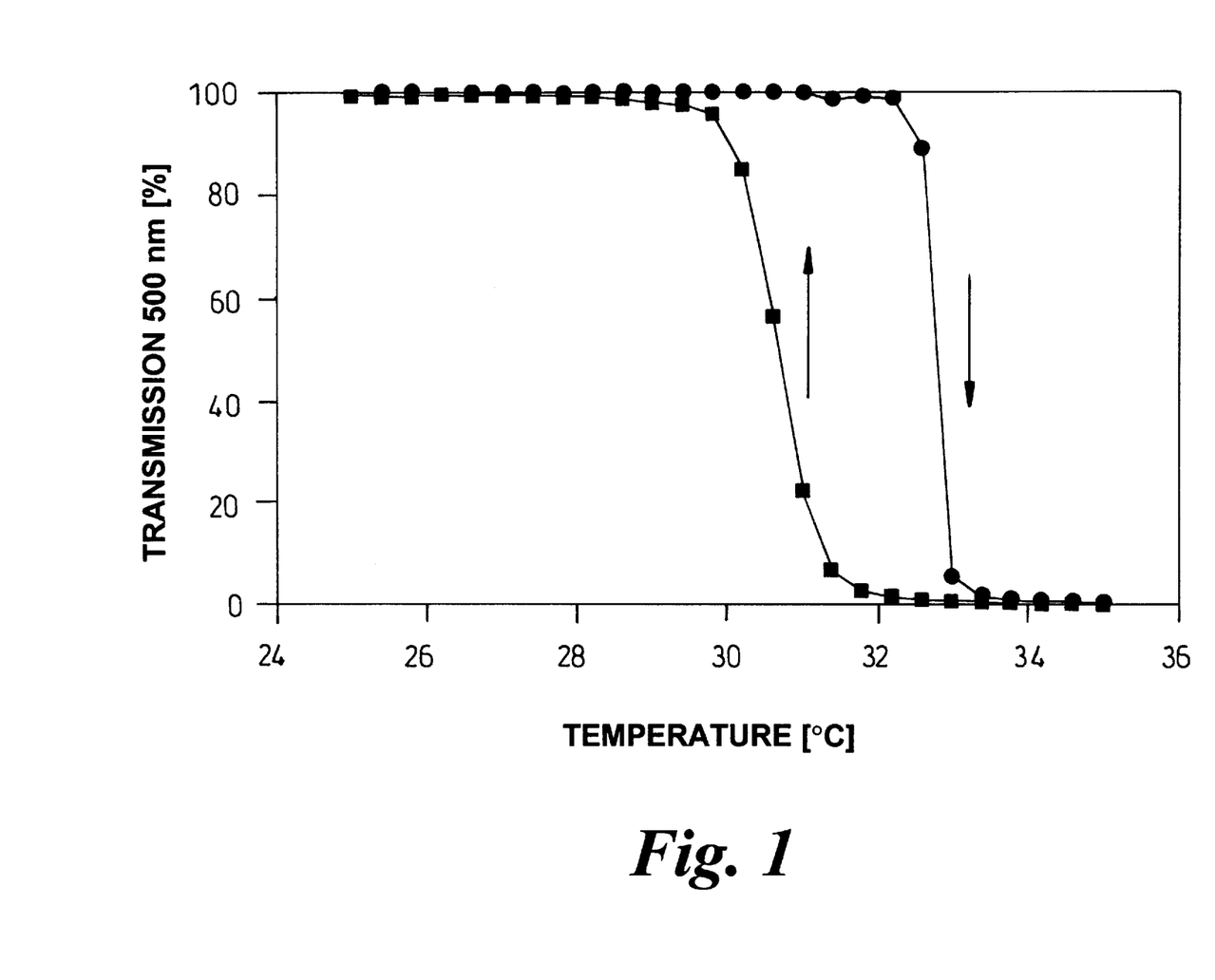
FIG. 1: Precipitation hysteresis of Polymer R1 synthesized by radical polymerization in the presence of the chain transfer agent MPA.
Figure 2:
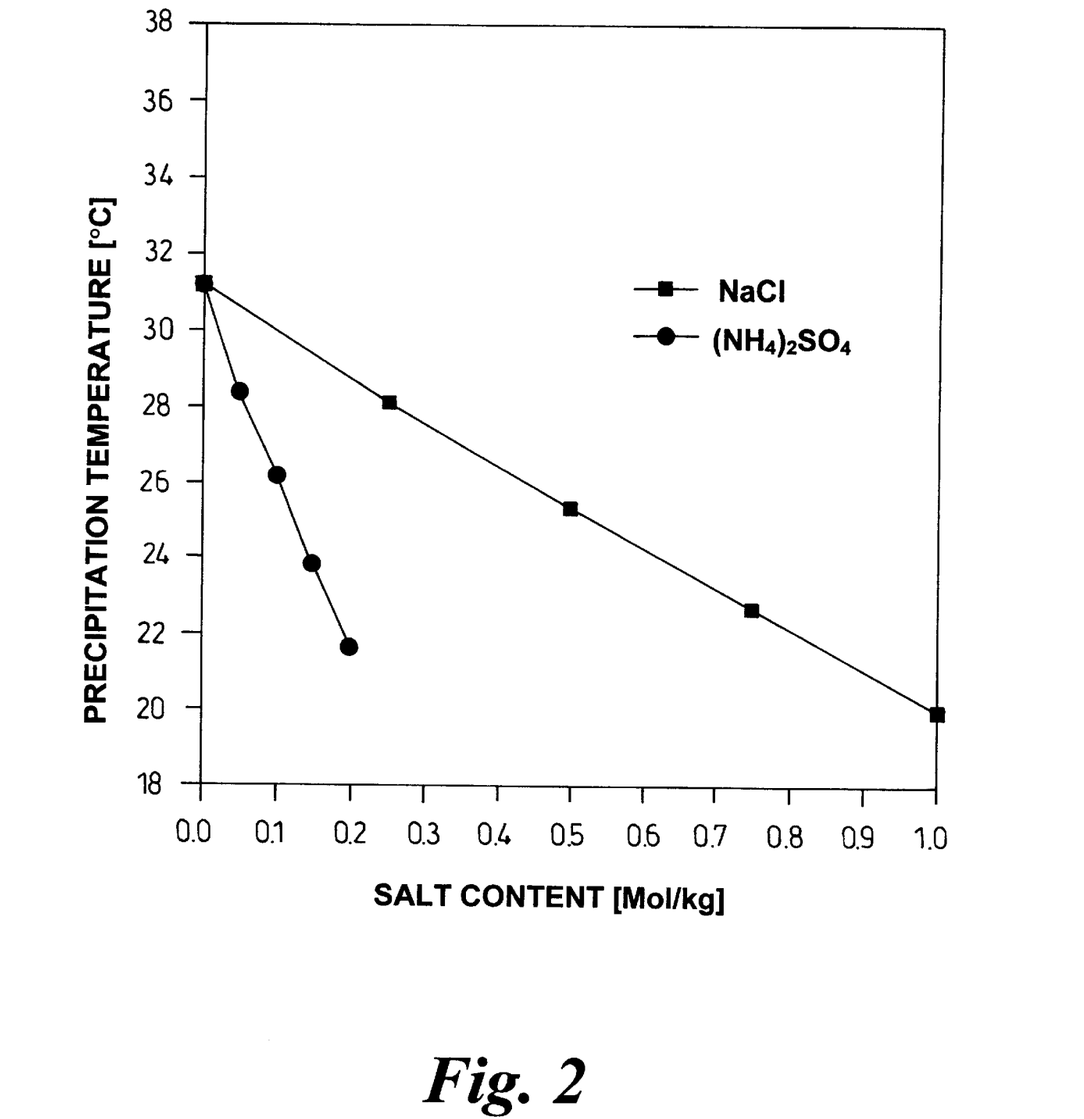
FIG. 2: Precipitation temperature of aqueous solutions of polymer R100 as a function of the solution's respective NaCl and $(NH_4)_2SO_4$ content.

Both NaCl and $(NH_4)_2SO_4$ lowered the precipitation temperature for both of the investigated polymers. As expected, the effect is much more pronounced for $(NH_4)_2SO4$ than for NaCl, FIG. 2. To exclude all temperature effects, salt concentrations are given in mol/kg of solution rather than mol/L. For the large radical poly-DEA R100, the presence of either 1.0 mol/kg NaCl or 0.2 mol/kg $(NH_4)_2SO_4$ lowered the precipitation temperature of a 0.1% (w/w) solution by approximately 10° C. In addition, the critical temperature drops almost linearly as a function of the salt content.

Figure 3:
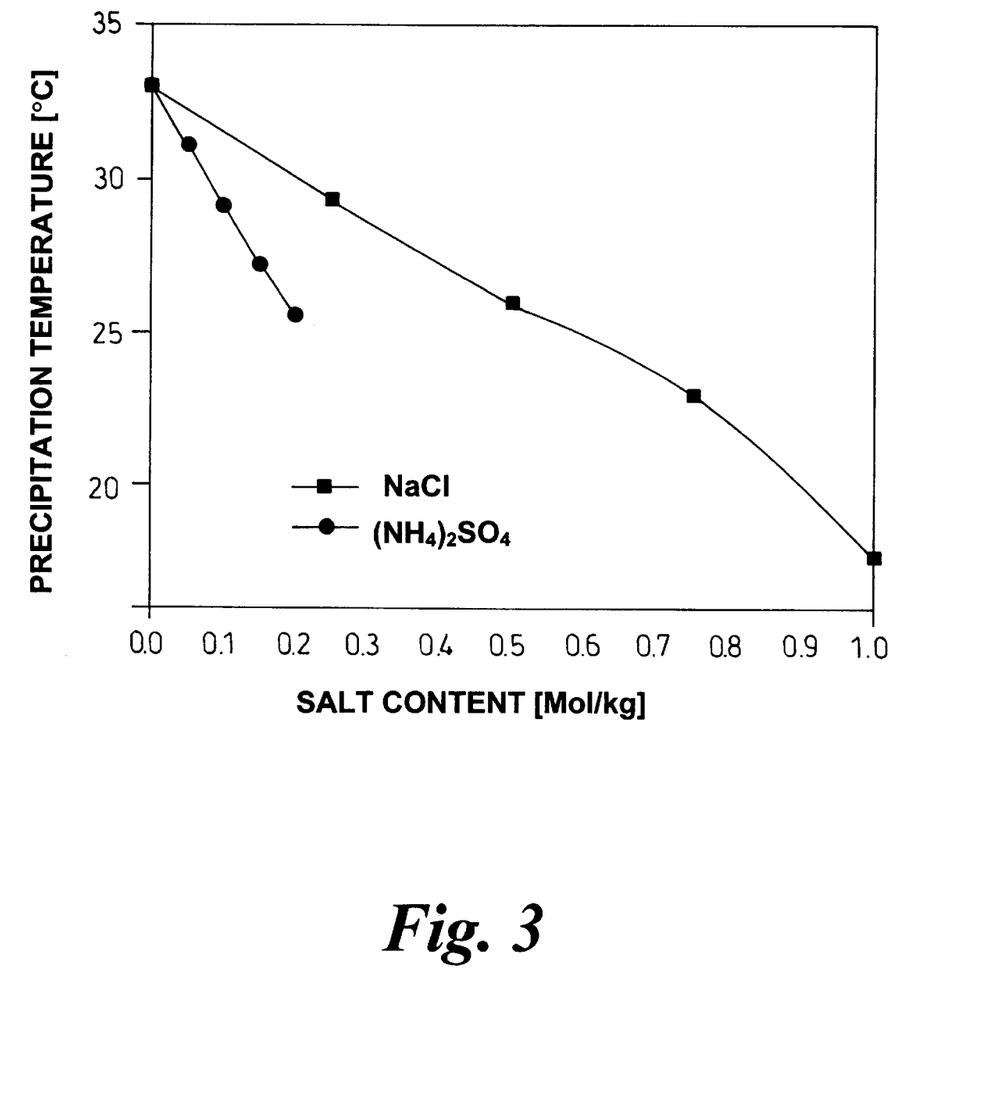
FIG. 3: Precipitation temperature of aqueous solutions of poly-NIPA N1 as a function of the solution's respective NaCl and $(NH_4)_2SO_4$ content.

In the case of a 1% (w/w) solution of poly-NIPA N1 the precipitation temperature is lowered by 15° C. in the presence of 1.0 mol/kg NaCl, while a 0.2 mol/kg concentration of $(NH_4)_2SO_4$ results in a lowering of the LCST by 8° C. In spite of the difference in chemical structure, the salt effect is apparently similar in heterotactic poly-NIPA and poly-DEA. Again, the drop in temperature depends almost linearly on the solution's salt content, FIG. 3.

Microcalorimetric investigation of the effect of molecular parameters on the LCST:

Modern high sensitivity differential calorimetry (HS-DOC) allows to investigate the thermodynamics of the phase transition process. In accordance with previous authors, a two state transition process was assumed for the coil globule transition of all investigated polymers. In order to investigate the thermodynamics of the phase transition only, all further reactions, which also might have a characteristic $\Delta H$ need to be avoided, theoretically including the association and precipitation leading to the macroscopically observed precipitation (cloud point). For example, it has been suggested that small amounts (>300 mg/L) of the surfactant SDS (sodium dodecyl sulfate) can be added to the solution, in order to prevent association/precipitation.

We found that an addition of 200 mg/L of SDS did indeed prevent precipitation. However, the HS-DOC results differed only within the uncertainty of the instrument when the $\Delta H$ was measured in the presence and the absence of the detergent. This led us to assume, that the $\Delta H$ of the association/precipitation is so small as to be negligible compared to the enthalpy of the phase transition. SDS concentrations above 300 mg/L did already exert an influence on the precipitation temperature. In order to avoid biasing the measurements by an SDS influence we chose to carry out the HS-DOC experiments described below without adding SDS to the samples.

In a second set of preliminary experiments it was verified (for R100 and R1) that neither the heating rate (1° C./min to 20° C./min) nor the polymer concentration (0.1% w/w to 5.0% w/w) influenced the DOC results ($T_{max}$, $T_{onset}$, calorimetric enthalpy). Contrary to prior art results, we also observed no influence of the heating rate on the van't Hoff enthalpy. We can thus assume the phase transition to be very close to equilibrium under these circumstances. Further experiments were carried out with a heating rate of 10° C./min and a polymer concentration of 1% w/w.

With the exception of the radical poly-DEA R1 and R2, the $T_{max}$ of the microcalorimetric endotherms is slightly below the turning point of the turbidity curve and corresponds more to the onset rather than the turning point of the macroscopically observed precipitation curve. This is hardly surprising, since we assume the calorimeter to record the actual phase transition, while the turbidity curves recorded with the photometer represent a secondary phenomenon, i.e. the final aggregation of the globules.

In spite of dramatic differences in the molecular mass, the transition widths tend to be similar and approximately 2.3° C. for most poly-DEA. The width of the endotherms is thus larger than that of the turbidity curves, which lay within a fraction of a degree, see above. In case of the poly-NIPA, the transition width for the low molecular mass substances N1 and N2 is significantly higher than for the high molecular mass polymers N100 and N200. It should also be noted that both the calorimetric and the van't Hoff enthalpies increase significantly with molecular mass in case of radical poly-NIPA, while they stay in the same order of magnitude in case of low and high molecular weight radical poly-DEA.

The measured calorimetric transition enthalpies are below the values found in the literature for similar polymers (i.e. 6.3 cal/g for poly-DEA and between 0.86 and 1.5 kcal/mol per repeating unit for poly-NIPA).

The addition of simple salt to poly-NIPA N200 had the expected (diminishing) effect on $T_{max}$. In order to explore the effect of a non-ionic but highly water-soluble substance, which in addition is found quite frequently in biotechnical matrices, glucose was added in a similar manner to aqueous solutions of the polymers. The effect on the precipitation temperature and on the phase separation thermodynamics was investigated. Low glucose concentrations resulted in an increase of the phase transition temperature, while this trend was reversed at higher concentrations.

Figure 4A:
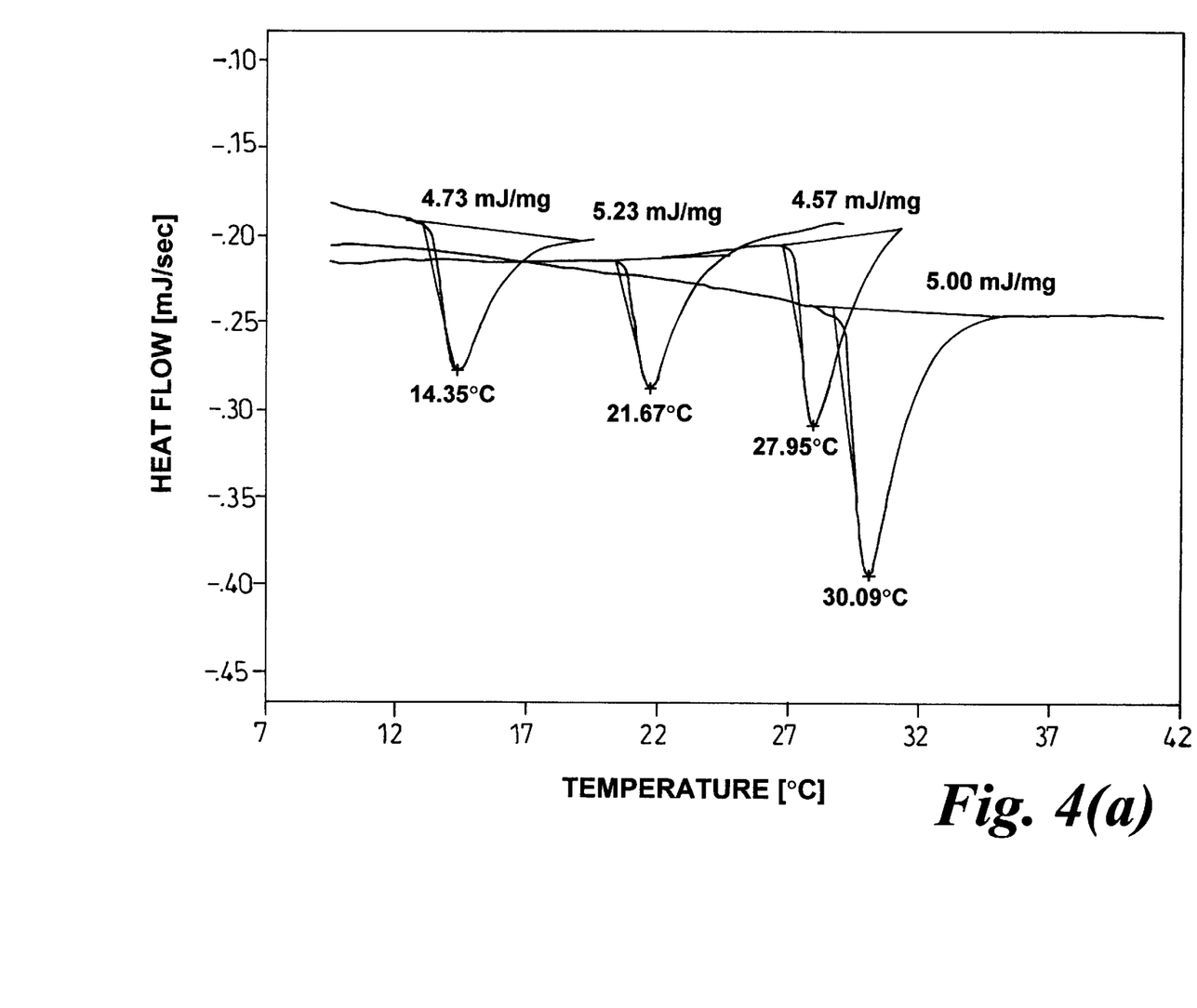
Figure 4B:
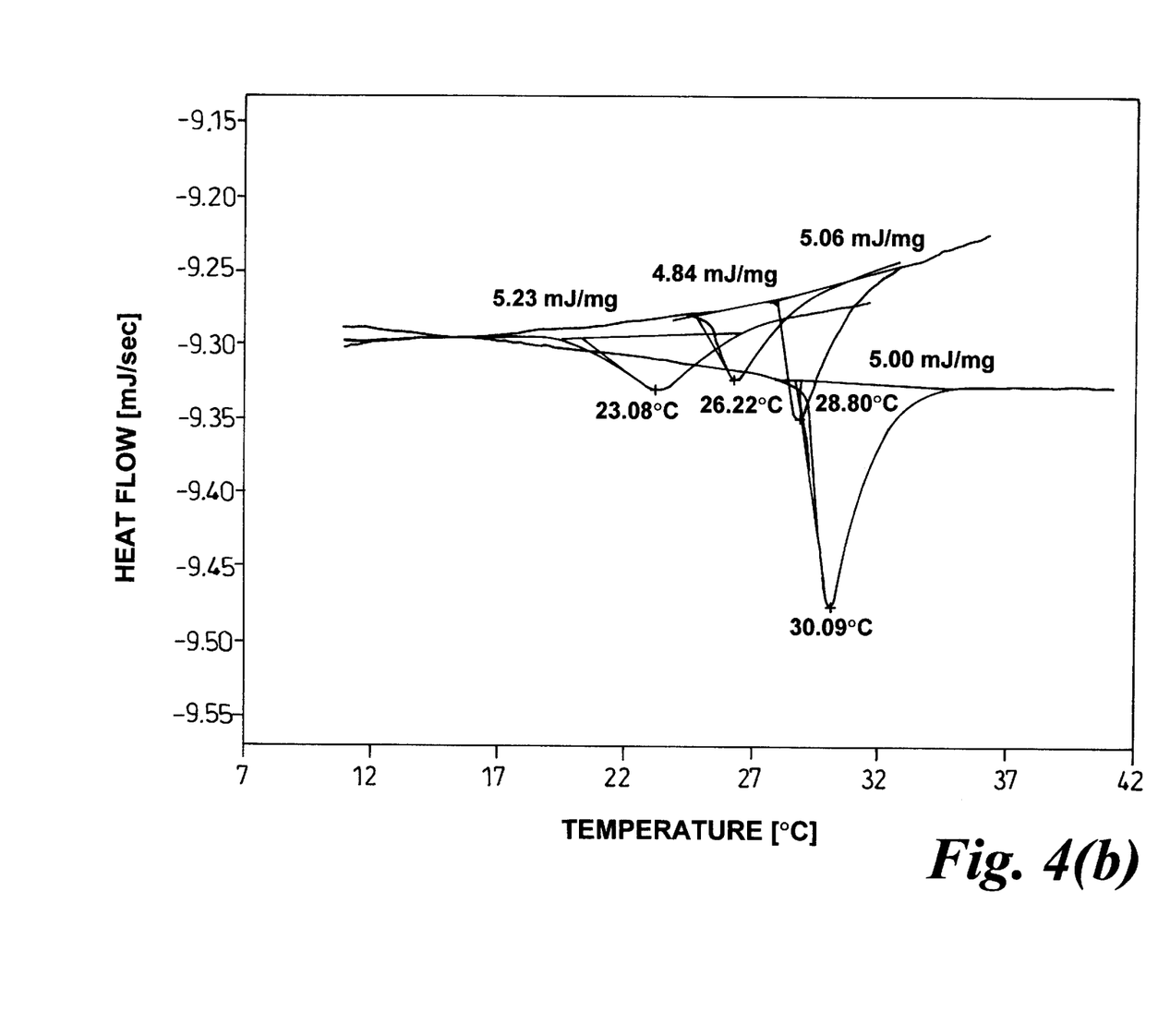

No clear trend could be observed for the transition widths at half height. While $T_{1/2}$ stays roughly the same in case of NaCl, $(NH_4)_2SO_4$, $CaCl_2$, and glucose addition, the endotherms measured for the highest $Na_2SO_4$ and $NaNO_3$ concentrations are almost twice as wide as those determined for the pure polymer solution, FIGS. 4a and b.

The calorimetric heat of transition was not influenced by the salt/glucose addition. The size of the cooperative unit decreases with increasing additive concentration, as evidenced by the change in $\Delta H_{eff}$. Due to the above-mentioned problems with the determination of the molecular weight of polymer N200, no $\Delta H_{cal}$ could be calculated. However, since the same polymer is used for all measurements, the ratio between $Q_{tr}$ and $\Delta H_{eff}$ is still correlated to the size of the cooperative unit. With the exception of the two cases characterized by exceptionally wide transition isotherms (i.e. the highest $Na_2SO_4$ and $NaNO_3$ concentrations), a correlation exists between the size of the cooperative unit and the temperature of the enthalpy minimum, $T_{max}$.

Avidin isolation process:

Poly-N-isopropylalkylacrylamides were prepared as indicated above in methanol with AIBN and cysteamine (HS—$CH_2$—$CH_2$—$NH_2$) as chain transfer agent (A:B:C= 100:0.6:6) at 60° C. for 21 hours. The polymers were twice precipitated from methanol in diethylether and finally precipitated once from acetone in hexane.

The polymers, e.g. poly-N-isopropylalkylacrylamide with an amino end group (average molar mass: 1660 g/mol and molar mass distribution: 1.04), were covalently coupled to iminobiotin by esterification via NHS activation forming an affinity macroligand with an LCST at 32° C. The coupling between affinity macroligand precursor and iminobiotin was verified by a modified HABA-test, which is described in the book of N. M. Green, "Methods in Enzymology", Vol. 18 A, p. 418 ff., Academic Press, 1970.

Polymer in water (pH 7):LCST at 32° C., precipitation temperature interval 1.5° C.

Polymer coupled with iminobiotin to from an AML in water (pH 7): LCST at 32° C., precipitation temperature interval 0.6° C.

Polymer coupled with iminobiotin to form an AML in buffer (pH 10.8) and in the presence of 1 M NaCl: LCST at 18.2° C., precipitation temperature interval 0.6° C.

Polymer coupled with iminobiotin to form an AML in buffer (pH 10.8) and in the presence of 1 M NaCl and avidin: LCST at 17.7° C., precipitation temperature interval 1.0° C. 20 mg AML was dissolved in 1.3 ml carbonate buffer (pH 10.8) and 0.25 mg/ml avidin. After incubation at 25° C., the AML-avidin complex was thermoprecipitated and centrifuged for 10 minutes at 13,000 g. HABA-test of the supernatant revealed that 75% of the avidin was isolated. By adding 1 M NaCl to the avidin-AML mixture, the percentage of avidin isolation could be increased to 90%. In both cases 100% of the bound (coprecipitated) avidin could be recovered in pure form after dissociation of the AML-avidin complex in acetate buffer (pH 4). The recovered avidin was 100% biologically active as determined in the following specificity test.

After adding 0.3 mg/ml lysozyme, 5 mg/ml lysozyme, a crude CHO culture medium containing 5% FCS (fetal calf serum) to the AML-avidin-buffer-NaCl mixture, 77%, 93% and 91% of the avidin were recovered respectively. Again, in all three cases, the avidin recovered after dissociation of the AML-avidin complex in acetate buffer (pH 4) was 100% active.

TABLE 1

Radical polymerization of N,N-diethylacrylamide (R1, R2) and N-isopropylacrylamide (N1, N2) in the presence of a chain transfer agent (MPA)

| Substance | Monomer:AIBN:MPA[1] | MPA | Yield |
|---|---|---|---|
| R1 | 100:1:5.0 | 0.137 mL | 62% |
| R2 | 100:1:2.5 | 0.069 mL | 56% |
| N1 | 100:1:5.0 | 0.154 mL | 91% |
| N2 | 100:0.5:4.5 | 0.477 mL | 84% |

[1]Molar ratio of monomer, radical starter, and chain transfer agent.

TABLE 2

MALDI MS data for the polymers and precipitation temperatures measured for the respective 1% (w/w) polymer solutions.

| Substance | $M_n$ [g/mol] | $M_n$ [g/mol] | D | Pn | Precipitation temperature |
|---|---|---|---|---|---|
| R1 | 1937 | 2394 | 1.236 | 15.3 | 32.7° C. |
| R2 | 1988 | 2335 | 1.174 | 15.7 | 32.5° C. |
| R100 | | | | | 31.4° C. |
| N1 | 2317 | 2735 | 1.180 | 20.5 | 33.2° C. |
| N2 | 1565 | 1774 | 1.13 | 13.8 | 33.4° C. |
| N100 | | | | | 29.9° C. |
| N200 | | | | | 32.2° C. |

References

The references mentioned herein are all expressly incorporated by reference.

1. R. Freitag, Current Trends in Polymer Science, 3, 63, (1998).
2. M. Eggert, R. Freitag, J. Polymer Science: Part A: Polymer Chem., 32, 803 (1994).
3. R. Freitag, T. Baltes, M. Eggert, J.Polymer Science: Part A: Polymer Chem., 32, 3019 (1994).
4. R. Freitag, T. Baltes, M. Eggert, K. Schugerl, U. Bahr, Bioseparation 4, 353 (1994).
5. M. Eggert, T. Baltes, F, Garret-Flaudy, R. Freitag, J. Chromatography A, 827 (1998) 269–280.
6. G. Chen, A. S. Hoffman, Bioconjugate Chem., 4, 509 (1993).
7. Z. Ding, G. Chen, A. S. Hoffman, Bioconjugate Chem., 7, 121 (1996).
8. Y. G. Takei, T. Aoki, K. Sanui, N. Ogata, T. Okano, Y. Sakurai, Bioconjugate Chem., 4, 42 (1993).
9. K. Hoshino, M.Taniguish, T. Kitao, S. Morohashi, T. Sasakura, Biotechnology and Bioengineering, 60(5), 568 (1998).

We claim:

1. An affinity macroligand (AML) which undergoes a binding interaction with a target substance in a mixture containing said target substance, said binding interaction having an affinity constant of dissociation, said affinity microligand comprising a ligand and reversibly water soluble polymer having a homopolymeric chain of repeating units represented by the formulae;

wherein:

L is a ligand;

R₁ and R₂ are independently selected from the group consisting of: hydrogen, —CH₃, —CH₂CH₃, —CH₂CH₂CH₃, —CH(CH₃)₂, —CH₂CH(CH₂CH₃)₂, —CH₂CH₂OCH₃, —(CH₂)₃OCH₃, —(CH₂)₃OCH₂CH₃, —(CH₂)₃OCH(CH₃)₂, —C(CH₃)₂CONHR₄ where R₄=—CH₃, —CH₂CH₃, —CH(CH₃)₂, —CH₂CH₂OCH₃, —(CH₂)₃OCH₃, —CH₂CH(OCH₃)₂, and —CH₂CH(OCH₂CH₃)₂;

R₃ is selected from the group consisting of pyrrolidinyl or piperidinyl and —O(CH₂)₃OH;

$x^1$ is the end group of the polymer through which the ligand is attached; and, wherein n is an integer between 5 and 40 and the polymer has:
(a) A number average molar mass (Mn) of less than 11,300 g/mol;
(b) A mass distribution (D) of less than 2.0; and,
(c) A narrow precipitation-solubility temperature (NPST) interval of less than 3° C.

2. The affinity macroligand of claim 1, wherein the affinity constant of dissociation of the interaction of the AML and the target substance is less than or equal to $10^{-7}$M.

3. The affinity macroligand of claim 1, wherein n is between 5 and 25.

4. The affinity macroligand of claim 1, wherein the number average molar mass of the polymer is between 500 g/mol and 7,000 g/mol.

5. The affinity macroligand of claim 1, wherein the mass distribution of the polymer is $\leq 1.3$.

6. The affinity macroligand of claim 1 wherein the NPST of the polymer is less than 2° C.

7. The affinity macroligand of claim 1, wherein the polymer is linear and has an average of about one reactive group per molecule.

8. The affinity macroligand of claim 1 wherein the polymer is selected from the group consisting of poly-N-isopropylalkylacrylamide, wherein R₁/R₂=hydrogen/isopropyl, poly-N,n-propylalkylacrylamide, wherein R₁/R₂=hydrogen/isopropyl, or poly-acryloylpyrrolidine, R₃=pyrollidinyl.

9. The affinity macroligand of claims, wherein the polymer is poly-acryloylpyrrolidine and number average molar mass of the polymer is less than 5,200 g/mol, wherein n is about 40.

10. A process for purifying a target substance from a liquid containing a mixture of the target substance and other materials, the process employing an affinity macroligand of claim 1 and comprising the steps of:
(a) contacting the AML with a liquid mixture under conditions in which the AML is soluble and the ligand can hind to the target substance;
(b) causing the AML to precipitate by changing the temperature of the liquid mixture to above its lower critical solution temperature or adding a salt or other cosolute, or by a combination of said temperature change and salt or other cosolute addition;
(c) separating the precipitated AML from the mixture; and,
(d) recovering the target substance from the AML.

11. The process of claim 10 which further comprises adding polymer to the liquid mixture to promote precipitation of the AML.

12. The process of claim 11 which further comprises the step of formulating the target substance in a composition.

13. A process for preparing an affinity macroligand (AML) of claim 1, the process comprising:

reacting a ligand L with a reversibly water soluble polymer having a homopolymeric chain of repeating units represented by the formulae:

wherein:

R₁ and R₂ are independently selected from the group consisting of: hydrogen, —CH₃, —CH₂CH₃, —CH₂CH₂CH₃, —CH(CH₃)₂, —CH₂CH(CH₂CH₃)₂, —CH₂CH₂OCH₃, —(CH₂)₃OCH₃, —(CH₂)₃OCH₂CH₃, —(CH₂)₃OCH(CH₃)₂, —C(CH₃)₂CONHR₄ where R₄=—CH₃, —CH₂CH₃, —CH(CH₃)₂, —CH₂CH₂OCH₃, —(CH₂)₃OCH₃, —CH₂CH(OCH₃)₂, and —CH₂CH(OCH₂CH₃)₂;

R₃ is selected from the group consisting of pyrrolidinyl or piperidinyl and —O(CH₂)₃OH; and, wherein n is an integer between 5 and 40 and the polymer has:
(a) A number average molar mass (Mn) of less than 11,300 g/mol;
(b) A mass distribution (D) of less than 2.0; and,
(c) A narrow precipitation-solubility temperature (NPST) interval of less than 3° C.; and wherein, wherein X is a group which is capable of reaction with a ligand to form the AML.

14. The process of claim 13, wherein the reactive group X is selected from the group consisting of: —S—(CH₂)ᵧ—COOH, —S—(CH₂)ᵧ—CHO, —S—(CH₂)ᵧ—NH₂, —S—(CH₂)ᵧ—OH, —S—(CH₂)ᵧ—SH, —S—(CH₂)ᵧ—CH₃, and their isomers, where y is an integer between 1 and 4.

15. The AML of claim 1, wherein the ligand is selected from the group consisting of:
(a) An antibody, an antigen, an antibody fragment or an antigen fragment;
(b) An enzyme, a co-enzyme, a substrate or an enzyme inhibitor;
(c) A group specific ligand;
(d) A polypeptide, an oligopeptide or an amino acid;
(e) A hormone, a receptor, an inhibitor, an effector or a co-factor;
(f) A sugar, a polysaccharide or a lipid;
(g) A vitamin, biotin or a biotin derivative;
(h) A cell or a cell surface receptor;
(i) A chelating agent; and (j) A nucleic acid molecule, an oligonucleotide, a chemical analog of a nucleic acid molecule or a chemical analog of an oligonucleotide.

16. The affinity macroligand of claim 13 wherein the affinity constant of dissociation of the interaction of AML and the target substance is less than or equal to $10^{-7}$ M.

17. The process of claim 10, wherein the AML is precipitated by changing the temperature of the liquid mixture to above its lower critical solution temperature and adding a salt or other cosolute.

* * * * *